(12) United States Patent
Sabin

(10) Patent No.: US 8,317,840 B2
(45) Date of Patent: Nov. 27, 2012

(54) SURGICAL METHOD FOR IMPLANTING A PERMANENT PERCUTANEOUS ELECTRICAL CONNECTION DEVICE

(75) Inventor: Pierre Sabin, Paris (FR)

(73) Assignee: Plugmed Heart (FR)

( * ) Notice: Subject to any disclaimer, the term of this patent is extended or adjusted under 35 U.S.C. 154(b) by 470 days.

(21) Appl. No.: 12/631,161

(22) Filed: Dec. 4, 2009

(65) Prior Publication Data
US 2011/0137357 A1    Jun. 9, 2011

(51) Int. Cl.
*A61B 17/88* (2006.01)
(52) U.S. Cl. ..................... 606/281; 604/175
(58) Field of Classification Search ............... 128/898; 604/175; 606/32, 34, 86 R, 281; 607/50–51, 607/116; 623/23.49
See application file for complete search history.

(56) References Cited

U.S. PATENT DOCUMENTS

| 5,873,368 | A | 2/1999 | Sabin | |
|---|---|---|---|---|
| 6,712,851 | B1 * | 3/2004 | Lemperle et al. | 623/16.11 |
| 6,840,919 | B1 * | 1/2005 | Håkansson | 604/175 |

FOREIGN PATENT DOCUMENTS

| FR | 2853248 A1 | 10/2004 |
|---|---|---|
| WO | 2004/089463 A2 | 10/2004 |

OTHER PUBLICATIONS

Sabin, Rev. Laryngol. Othol. Rhinol., 118(5); 335-342 (1997).
Sabin, Rev. Stomatal. Chir. Mexillofac, 100(3); 123-131 (1999).
* cited by examiner

*Primary Examiner* — Kevin T Truong
*Assistant Examiner* — Larry E. Waggle, Jr.
(74) *Attorney, Agent, or Firm* — Lerner, David, Littenberg, Krumholz & Mentlik, LLP

(57) ABSTRACT

The invention relates to a surgical method for positioning a permanent percutaneous electrical connection device in a receiving bone site of a patient, the patient being a human being or an animal, and the device comprising, on the one hand, a plate-implant integrating at least one fixed electrical connection port and, on the other hand, a percutaneous electrical connection abutment designed to be coupled to the electrical connection port, the method comprising the following successive steps:
  step of preparing the receiving bone site, during which:
    the cutaneous plane facing the receiving bone site is incised, then
    the periosteum of the receiving bone site is incised and detached and then reclined to clear the bone structure, then
    the bone structure is hollowed out so as to form a cavity in which the plate-implant is to be impacted;
  step of impacting the plate-implant into the cavity formed in the receiving bone site, during which:
    the plate-implant is anchored in the cavity formed in the receiving bone site, then
    bone fragments are positioned to cover the plate-implant except in the area of the fixed electrical connection port, then
    said bone fragments are covered with a membrane to keep the bone fragments in position so as to ensure guided bone regeneration, said membrane being affixed to the bone structure on one part and to the plate-implant on another part in order to hold the bone fragments in position.

10 Claims, 17 Drawing Sheets

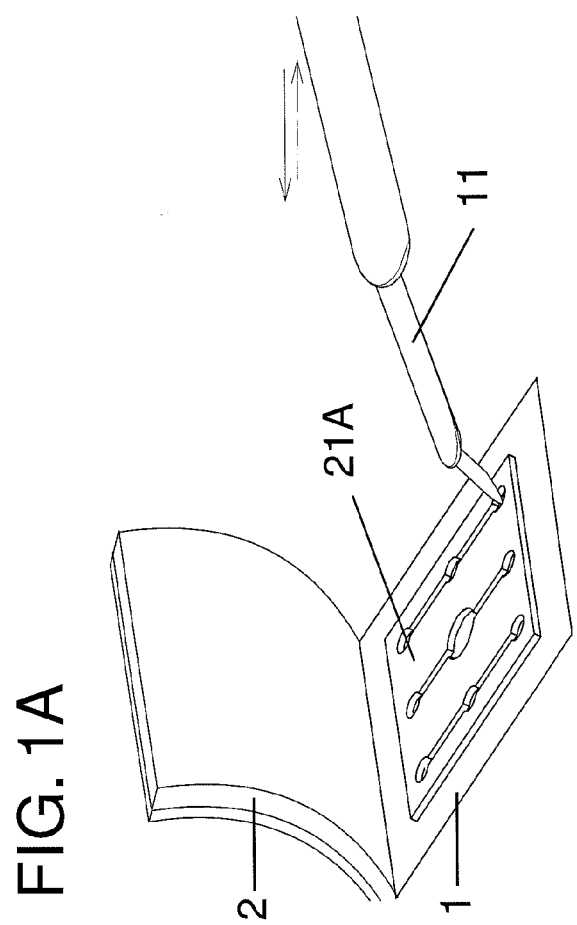

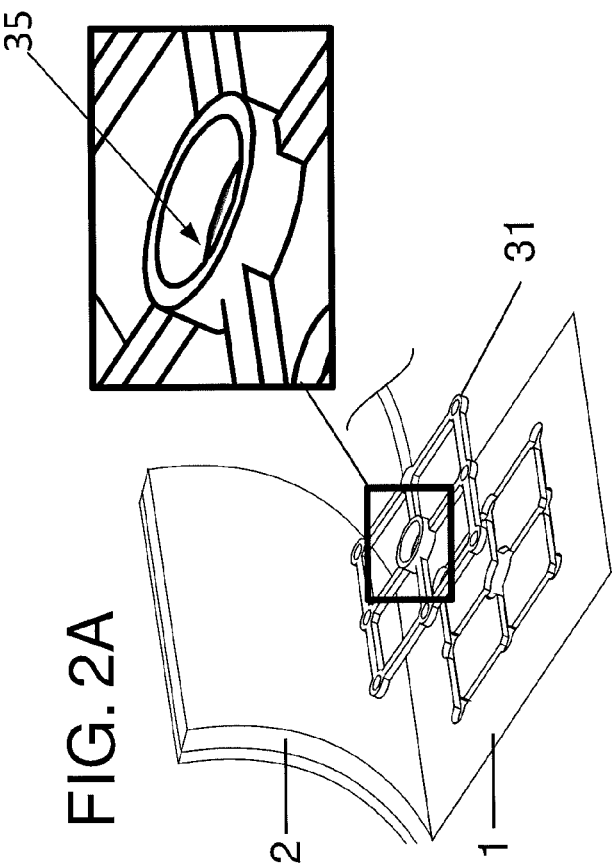

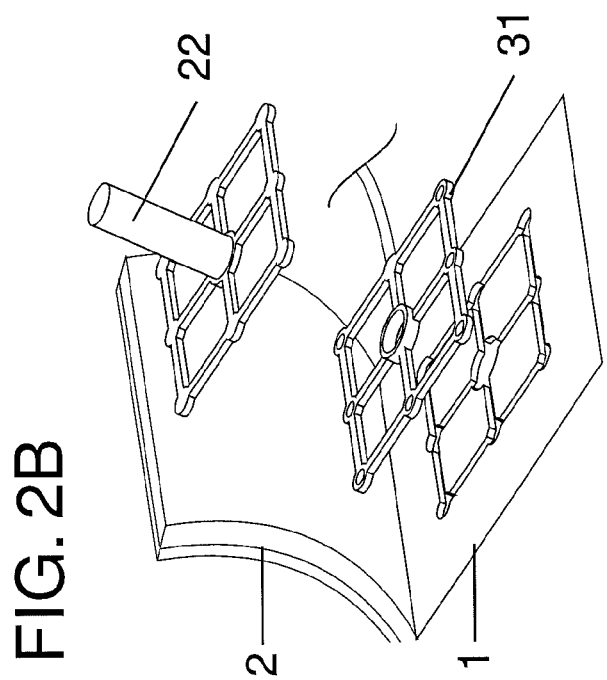

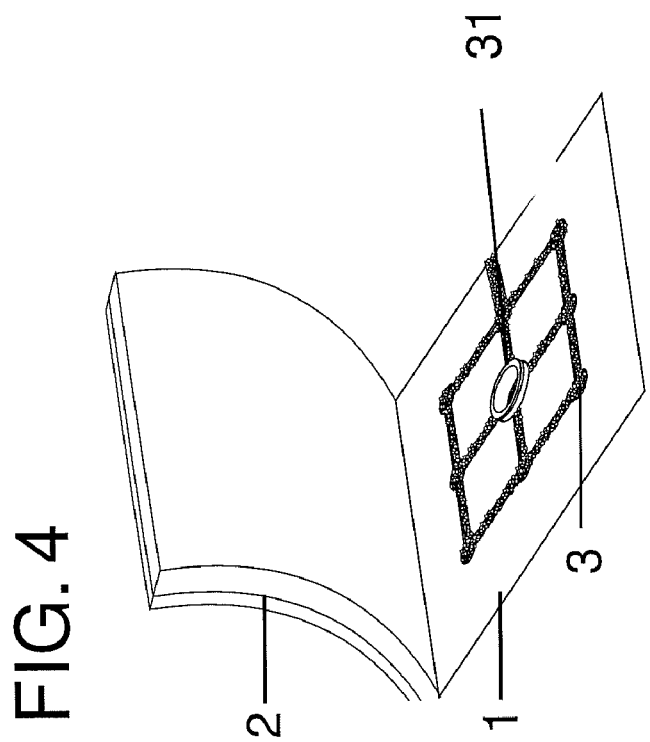

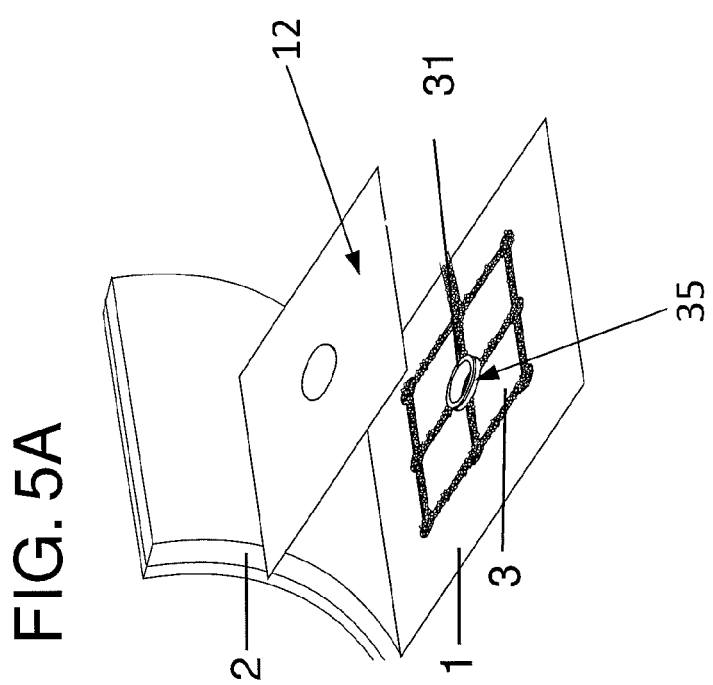

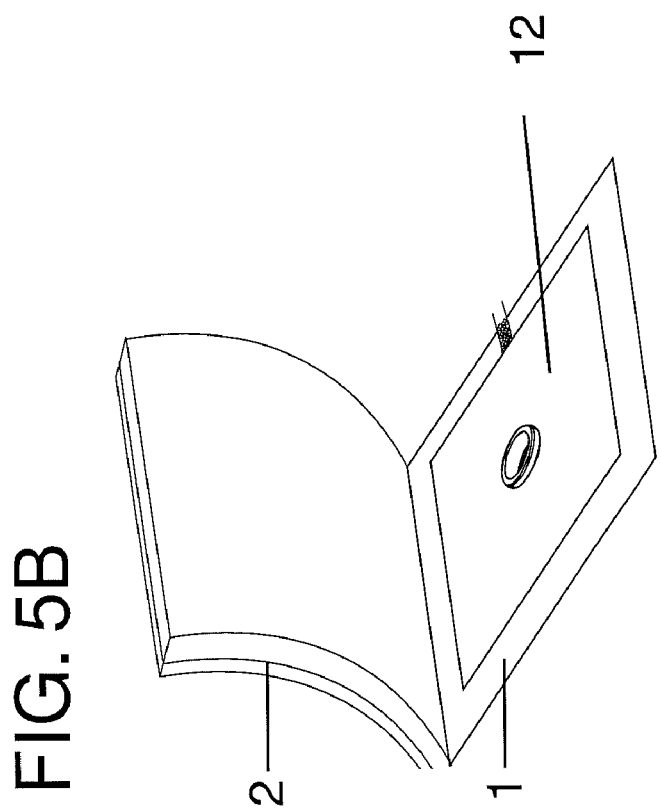

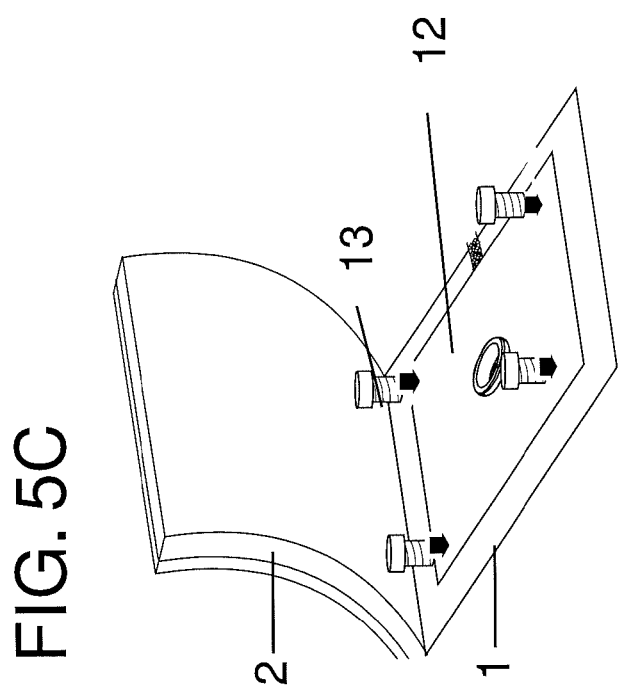

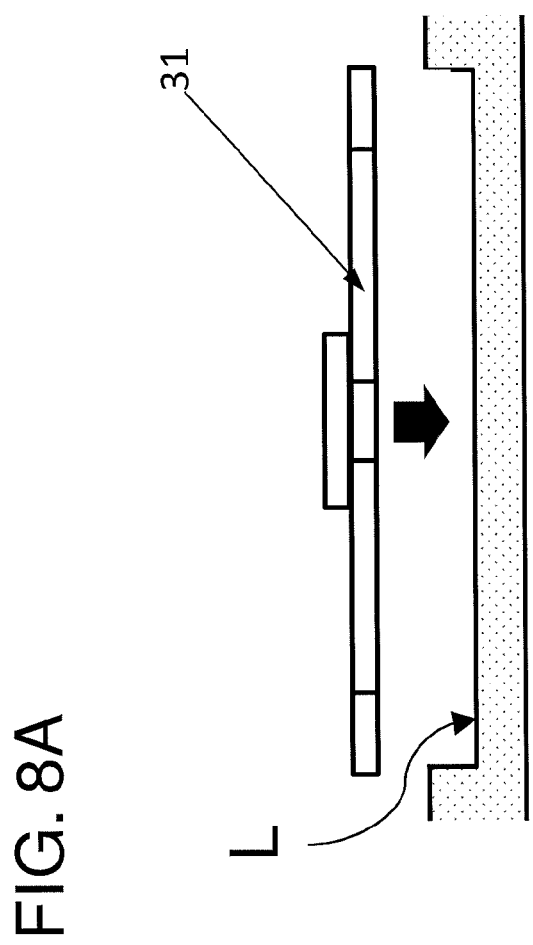

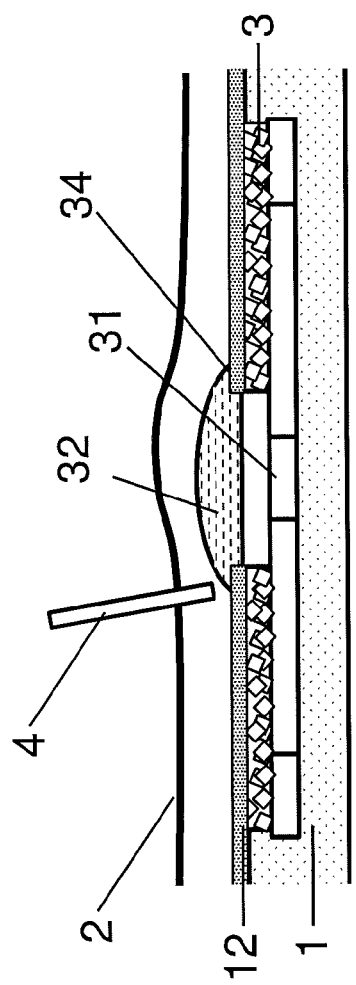

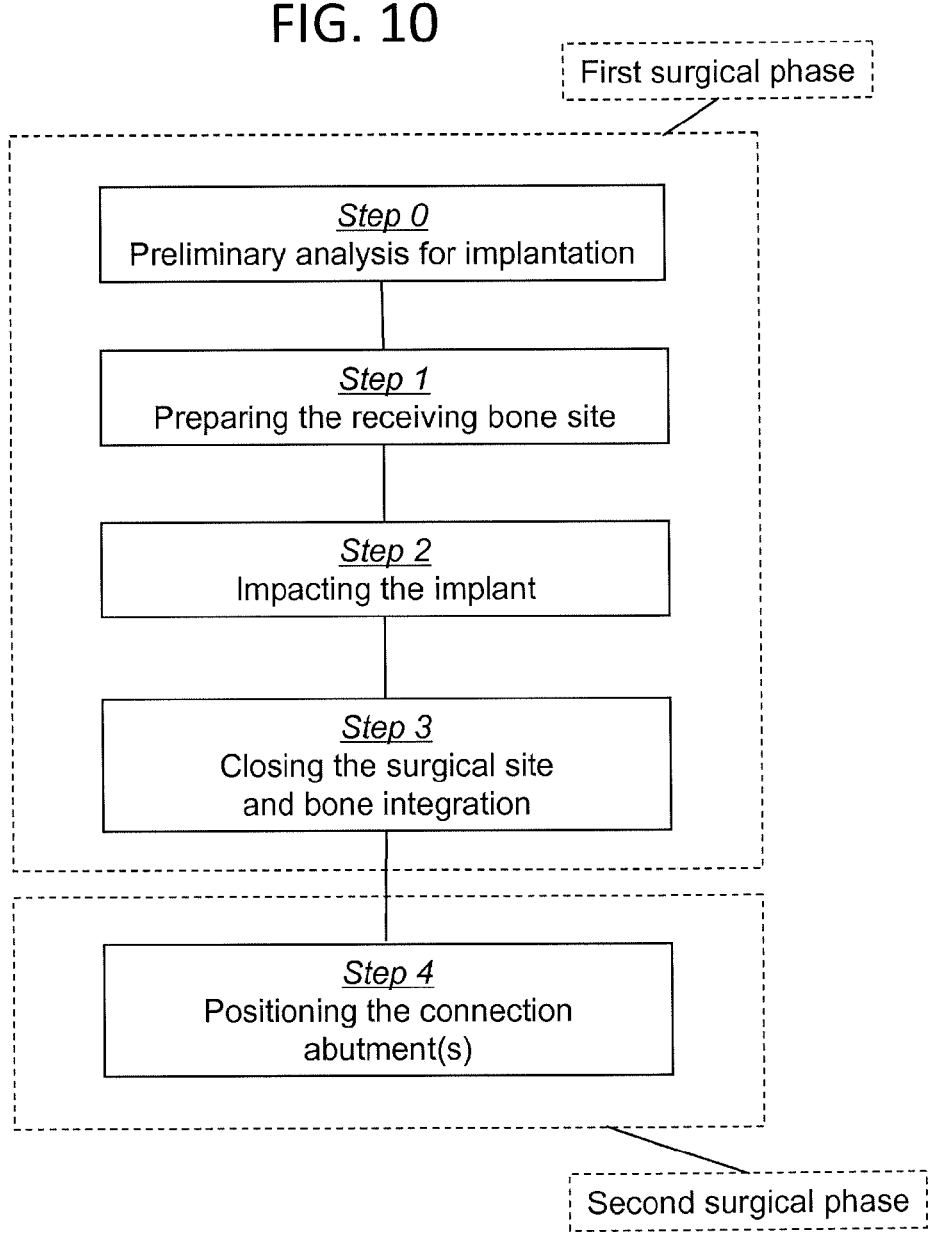

SURGICAL METHOD FOR IMPLANTING A PERMANENT PERCUTANEOUS ELECTRICAL CONNECTION DEVICE

FIELD OF THE INVENTION

The present invention concerns the field of permanent percutaneous electrical connection devices, and relates more precisely to the surgical method for implanting such device in a patient, whether the patient is a human being or an animal.

BACKGROUND OF THE INVENTION

The development of brain/computer interface research, neuroprostheses and functional electrical stimulation, as well as the development of electrical equipment designed to be implanted in the body of a patient to correct a defect in a natural organ, necessitates being able to transmit the electrical energy and/or signals required by this equipment, from a source of energy or information outside the patient to the inside of this patient's body, or to collect data such as electrical signals emanating from the defective natural organ and/or electrical equipment implanted in the patient and designed to alleviate these defects.

There exist supply systems without direct equipment contact, called transcutaneous connection, that use energy transmission by transformer effect, by induction or transmission of electromagnetic microwaves.

There are also supply techniques with direct percutaneous electrical connection, some of which use a one-piece biconical device with one base affixed to a bone substrate by osteosynthetic screws, and another base outside the plane of the skin, as well as a narrow part where the plane of the skin is crossed. These hollow devices allow the passage of flexible electrical connection means located in the body to an external removable electrical socket. Other solutions cross the plane of the skin directly, generally at the abdomen, such as for example assisted circulation (cardiac) devices.

Finally, there are permanent percutaneous electrical connections (PPEC or CEPP for the French expression "Connexion électrique percutanée permanente"), arising from extraoral implantology, made up of a plate-implant which is positioned in a first surgical phase, onto which percutaneous electrical abutments are screwed in a second surgical phase, for transmission of electrical signals and/or energy and possibly mechanical abutments for mechanical support of the removable connector. This type of connection respects the recommendations and principles for installing conventional extraoral implants, which are designed to permit the skin to be crossed by support abutments for maxillofacial prostheses, so that these permanent percutaneous electrical connections are very reliable, since they arise from a proven technology.

Thus, the conventionally used surgical method for implanting such permanent percutaneous electrical connection devices consists of two surgical phases. The first phase consists of affixing a plate-implant onto a bone by using osteosynthetic screws allowing permanently fixation of the plate-implant serving as a base for the device. Once the osteosynthetic screws have been correctly integrated in the receiving bone site, after several months, the second surgical phase can be performed, during which the percutaneous abutment is positioned on the base. The external appliances will be connected to this abutment by means of a removable external connector, so as to be electrically connected through the skin with sensors and other equipment implanted permanently in the body, i.e. in the organism of the patient.

One objective of the present invention is to propose a new surgical method for implanting permanent percutaneous electrical connection devices that allows stronger anchoring of the device and improved comfort for the patient.

BRIEF SUMMARY OF THE INVENTION

To this end is proposed a surgical method for positioning a permanent percutaneous electrical connection device in a receiving bone site of a patient, the patient being a human being or an animal, and the device comprising, on the one hand, a plate-implant integrating at least one fixed electrical connection port and, on the other hand, a percutaneous electrical connection abutment designed to be coupled to the electrical connection port, the method comprising the following successive steps:
  step of preparing the receiving bone site, during which:
    the cutaneous plane facing the receiving bone site is incised, then
    the periosteum of the receiving bone site is incised and detached and then reclined to clear the bone structure, then
    the bone structure is hollowed out so as to form a cavity in which the plate-implant is to be impacted;
  step of impacting the plate-implant into the cavity formed in the receiving bone site, during which:
    the plate-implant is anchored in the cavity formed in the receiving bone site, then
    bone fragments are positioned to cover the plate-implant except in the area of the fixed electrical connection port, then
    said bone fragments are covered with a membrane to keep the bone fragments in position so as to ensure guided bone regeneration, said membrane being affixed to the bone structure on one side and to the plate-implant on the other side in order to hold the bone fragments in position.

Some preferred but non-limiting aspects of this surgical method, taken alone or in combination, are the following:
  during the receiving bone site preparation step, the bone fragments produced when the bone structure is hollowed out to form the cavity are collected, in order to use these bone fragments during the plate-implant impaction step.
  the step of preparing the receiving bone site is done with permanent irrigation to limit heating of the receiving bone site.
  the bone structure is hollowed out by using a template that enables hollowing a cavity with a form corresponding to the plate-implant outline, said cavity having smaller dimensions so as to provide primary anchoring of the implant-plate in the cavity by cooperation of the corresponding walls.
  the membrane covering the bone fragments is affixed to the bone structure on one side by osteosynthetic screws positioned at the membrane periphery and affixed to the plate-impact on the other side, via a thin metal plate pressing the membrane around the protective caps positioned on the fixed electrical connection port.
  an impaction tool is used with a support surface having a form complementary to the form of the upper surface of the plate-implant, so as to anchor the plate-implant in the bone cavity without deforming said plate-implant.
  the surgical method further comprises a step of bone integration consisting of covering the membrane and the plate-implant by the periosteum, and then by the skin flap of the patient, after a hematoma drain has been positioned.

the surgical method comprises a second surgical phase performed 3 to 4 months after the first surgical phase for positioning the plate-implant, said second surgical phase comprising the following successive steps:
  removal of the membrane ensuring guided bone regeneration,
  removal of a protective cap positioned on the fixed electrical connection port of the plate-implant, then replacement of said protective cap with the percutaneous electrical connection abutment.
the permanent percutaneous electrical connection device is connected with one or more elements located inside the organism of the patient.
the permanent percutaneous electrical connection device is also connected with one or more elements located outside the organism of the patient.

BRIEF DESCRIPTION OF THE DRAWINGS

Other characteristics and advantages of the invention will appear from the following description, which is purely illustrative and non-limiting and should be read with regard to the attached drawings.

FIG. 1A and FIG. 1B each illustrate a perspective view of a bone structure being hollowed out with the help of a template;

FIG. 2A illustrates a perspective view of a permanent percutaneous electrical connection device relative to the bone structure;

FIG. 2B illustrates a perspective view of an impaction tool relative to the permanent percutaneous electrical connection device of FIG. 2A;

FIG. 4 illustrates a perspective view of the permanent percutaneous electrical connection device of FIG. 3 being covered by bone fragments;

FIG. 5A illustrates a perspective view of a membrane relative to the permanent percutaneous electrical connection device of FIG. 4;

FIG. 5B illustrates a perspective view of the membrane of FIG. 5A covering the permanent percutaneous electrical connection device;

FIG. 5C illustrates a perspective view of the membrane of FIG. 5B being fixed by osteosynthetic screws;

FIG. 8A illustrates a side view of the permanent percutaneous electrical connection device relative to a prepared osseous site surrounded by bone walls;

FIG. 8B illustrates a side view of the permanent percutaneous electrical connection device positioned in the osseous site of FIG. 8A;

FIG. 10 is a schematic illustration of a surgical implantation method according to an embodiment of the invention.

DETAILED DESCRIPTION

The description that follows discloses the surgical method for implanting a permanent percutaneous electrical connection device in a patient; this patient can be a human being or an animal.

Figure 9:
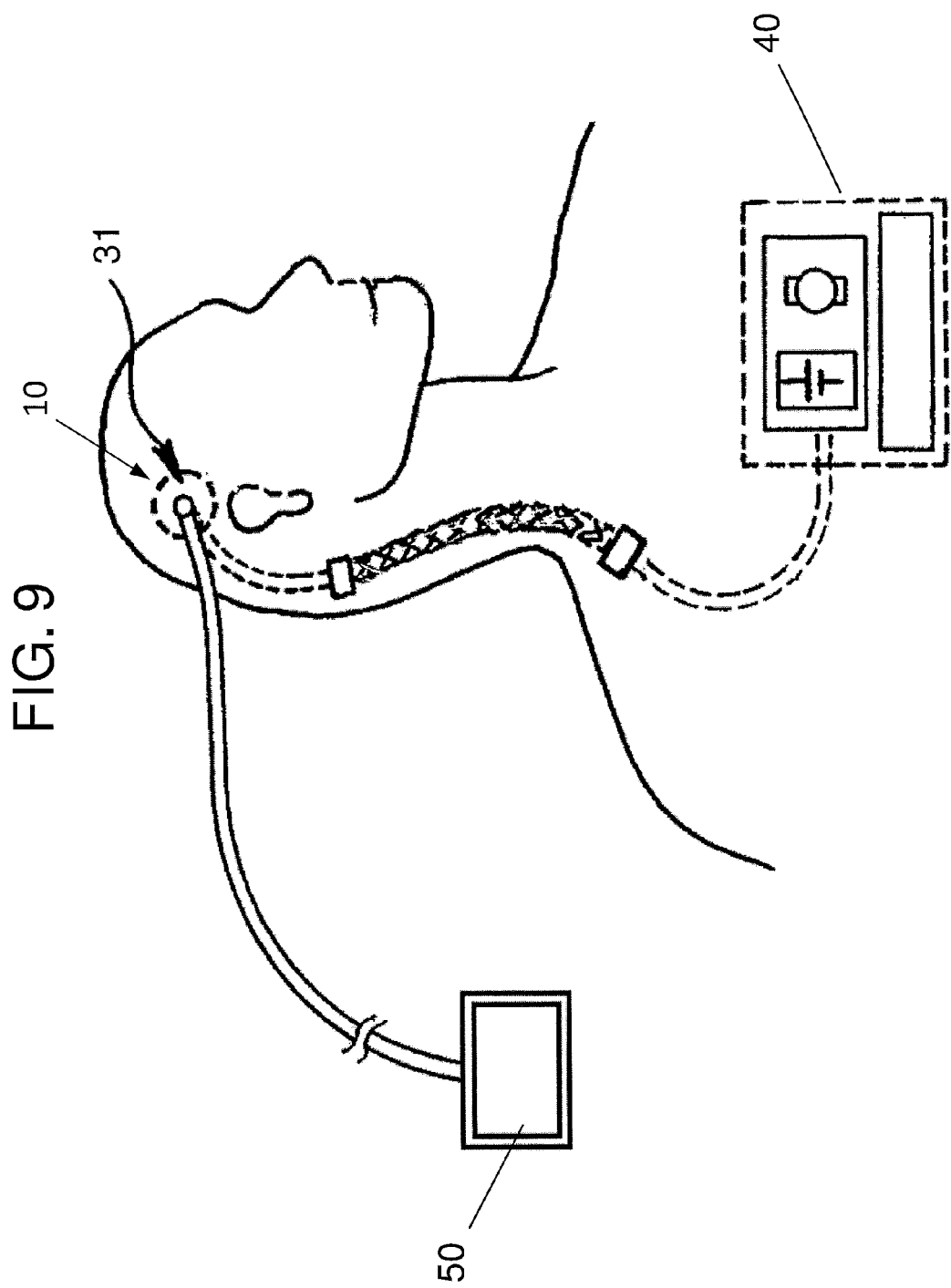
FIG. 9 illustrates the permanent percutaneous electrical connection device connected to elements internal and external to a patient.

As illustrated in FIG. 9, a permanent percutaneous electrical connection device 10, designed to electrically connect an entity 40 inside a human or animal body to an entity 50 outside said body, generally comprises a support plate, called plate-implant 31, provided to be affixed to a bone of said body, and percutaneous electrical connection means, these percutaneous electrical connection means comprising (i) fixed electrical connection means integrated into the support plate, and (ii) removable electrical connection means provided to be electrically coupled to said fixed electrical connection means and respectively connected to said flexible electrical connection means. Preferably, mechanical percutaneous connection means are further provided, also comprising fixed mechanical connection means integrated into the support plate, and removable mechanical connection means provided to be coupled mechanically to said fixed mechanical connection means. According to a preferred aspect, these percutaneous electrical and mechanical connection means are combined.

An entity 40 located inside the body, or internal entity 40, means here any electrical appliance consuming or producing electrical energy, possibly designed to receive electrical command or monitoring signals, and any measuring or sensor equipment provided to generate electrical signals.

An entity 50 outside the body, or external entity 50, means here any equipment close to or far from the body, provided to supply electrical energy and/or control or monitoring signals, or to receive signals generated by any sensor or electric appliance inside the body and/or electrical energy generated by equipment inside the body.

For more specific examples of permanent percutaneous electrical connection devices, refer to U.S. Pat. No. 5,873,368 published on Feb. 23, 1999, PCT Application WO 2004/089463 published on Oct. 21, 2004, and French Patent Application FR 2,853 248, published on Oct. 8, 2004. The content of these documents is completely incorporated by reference in the present description.

The principle of permanent percutaneous electrical connection (PPEC or CEPP) consists of fitting an electrical connector to a abutment and an implant similar to conventional extraoral components, in which a percutaneous abutment is affixed onto an extraoral implant that supports it, so that the abutment establishes a permanent communication between the inside and the outside of the body. The addition of an electrical connector to an implant provided with an abutment transforms a conventional permanent percutaneous connection into a permanent percutaneous electrical connection. The electrical connector is housed inside the abutment, and is connected to the implant from where the subcutaneous electrical wires arise.

As indicated above, the permanent percutaneous electrical connection device has two main parts: the implant affixed to the bone (plate-implant) and the percutaneous abutment crossing the skin. The plate-implant is generally a plate made in Titanium (T40) or Zirconia, preferably circular, in the center of which a bearing element for electrical connection is found, i.e. the fixed electrical connection port. One of the arms of the plate-implant is hollow and allows electrical wires to be passed through leading to the bearing element. This electrical port can comprise up to 8 female DIN contacts. The percutaneous electrical connection abutment, generally having the form of a cylinder of several millimeters diameter is joined to the port by direct screwing. The internal part of the abutment receives the electrical connector, thus forming a socket for the permanent percutaneous electrical connection. This connector can comprise up to 8 male DIN contacts. For a simple stimulation, two wires are enough: one phase, one neutral; the plate can be grounded.

The surgical method described below concerns the implantation of equipment designed to remain permanently through the plane of the skin.

The surgical protocol for positioning a permanent percutaneous electrical connection device described below is based on the principles and method for positioning extraoral implants, in particular with regard with the two-step procedure, first positioning the implant and then positioning the abutment several months later, and also with regard to reduction of subcutaneous soft tissue.

The main feature of the implantation method proposed resides in the fact that the plate-implant is not simply affixed on the bone (for example by using osteosynthetic screws) as was the case for methods of the prior art, but this implant is truly integrated into the bone, that is to say, the plate-implant is osseointegrated.

This implantation method is further innovative in the way the plate-implant is osseointegrated in the bone. In fact, as can be seen in detail below, osseointegration is promoted by impacting the plate-implant, and then by covering the implant by bone fragments and a complementary healing membrane promoting bone proliferation and cooperation between the bone and the implant.

Such a technique had never been developed for the usual extraoral implantology protocols, where the extraoral implant generally has the form of a screw directly embedded by screwing (or impacted cylinders) or the form of a plate affixed with osteosynthetic screws.

The fact that the plate-implant is totally integrated into the bone by the method proposed allows better anchoring of the device overall, which is particularly advantageous since the device is designed to be positioned permanently. Such a plate-implant anchoring technique is much more reliable over the long term than simple fixation onto the bone.

This implantation technique is also particularly advantageous in that it allows reducing the discomfort experienced by the patient when the device is implanted. Indeed, the fact that the plate-implant is integrated into the bone, that is to say embedded in the bone, implies that there is no extra thickness at the implantation area, apart from the percutaneous electrical connection means.

The second phase of the method for permanently positioning the connection abutment for the permanent percutaneous electrical connection device is in itself identical to those already proposed, particularly in U.S. Pat. No. 5,873,368 published on Feb. 23, 1999.

General and Chronological Description of the Surgical Protocol

The proposed surgical methodology allows installing equipment for ensuring direct passage of electrical current from one side of the skin plane to the other, permanently and continually, with neither infection nor inflammation (excluding medical accident).

As indicated, positioning a permanent percutaneous electrical connection device is done in two successive surgical phases, to respect the basic principles of extraoral implantology. In the first phase, the inner part of a so-called plate-implant or implant device is positioned and impacted into the bone, and then the skin plane is closed. Bone healing around this implant takes place for several months, which is called osseointegration.

In a second phase, three to four months after the implant has been positioned and impacted to the bone, the percutaneous electrical connection is created.

The electrical continuity between the bone-anchored part of the permanent percutaneous electrical connection device, i.e. the plate-implant, and the implanted appliance (or the organ concerned) is established either when the implant is positioned, or when the percutaneous abutment is positioned during a second surgical phase.

In light of this general description, it is possible to describe a general and chronological protocol for positioning a permanent percutaneous electrical connection device according to the following successive steps.

Step 0 (Optional): Preliminary Analysis for Implantation

An optional but preferred preliminary step consists of examining the receiving bone site by imaging (scanning and/or x-ray), by a virtual simulated implantation, and then possibly by simulated implantation by means of a stereolithographic cranial model corresponding to the receiving bone site.

Step 1: Preparing the Receiving Bone Site

The surgical procedure for positioning the plate-implant must follow the rules common to all receiving bone sites for extraoral implants. In particular, the bone site must be approached while respecting the surrounding soft tissue, while limiting bleeding (for example with hemostasis by electrocoagulation), and by sufficiently clearing the receiving bone site so as to be able to use the ancillary equipment without injuring the adjacent soft tissue.

The approach for the skin incision may be bicoronal, by parietal arc-shaped incision, or by paramedian straight Y incision.

Figure 1B:
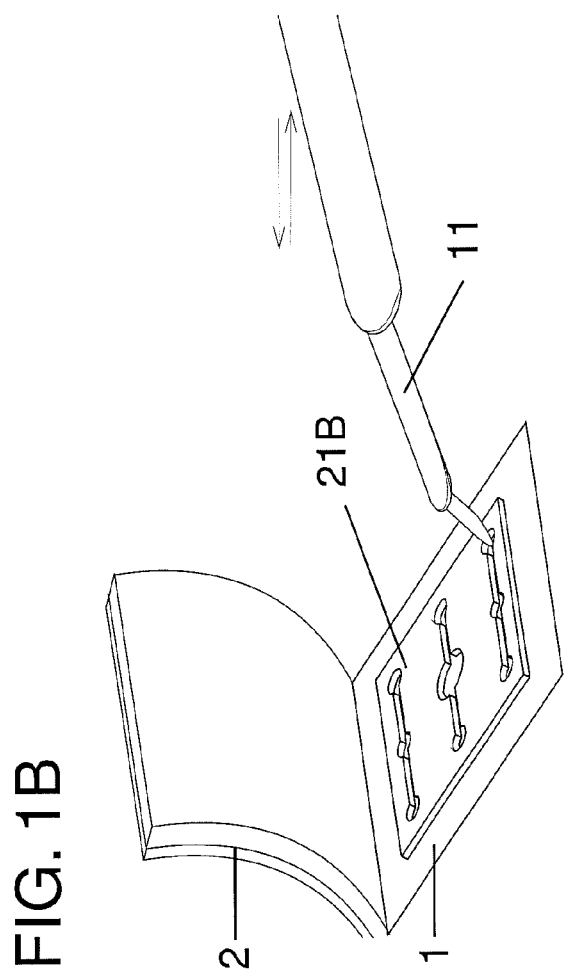

As shown in FIGS. 1A-1B, the periosteum 2 is then incised, detached and reclined (by reclined is meant bent or curved downward and/or backward) in order to clear a sufficient bone surface for positioning the future implant.

When this area for the future implant is cleared, it is necessary to hollow out the outer bone table receiving the plate-implant that will be positioned. The cavity which is hollowed out has preferably a shape similar to the shape of the plate-implant.

Various manual or mechanical means, enumerated later, for instance as illustrated in FIGS. 1A-1B, can be used to prepare the receiving bone site 1. Regardless of the cutting means 11 used, the bone fragments resulting from the preparation of the site 1 are preferably carefully collected to eventually be used later in the surgical procedure as described below.

Once the cavity designed to receive the implant has been hollowed out in the receiving bone site 1, the shape and dimension of such cavity are compared to a template 21A or 21B of the implant as shown in FIGS. 1A-1B, and any necessary rectifications are made. Such a template 21A or 21B can be used at the beginning of the hollowing operation to define the portion of the bone structure to be hollowed out.

Preferably, the cavity is hollowed out so as to essentially respect the plate-implant outline, while having slightly smaller dimensions so that the plate-implant can be naturally anchored in the cavity without any other means of fixation.

Step 2: Impacting the Implant

As shown in FIG. 2A, the plate-implant 31 is then positioned in the cavity created in the receiving bone site 1 with a shape complementary to the shape of the plate-implant 31.

Figure 3:
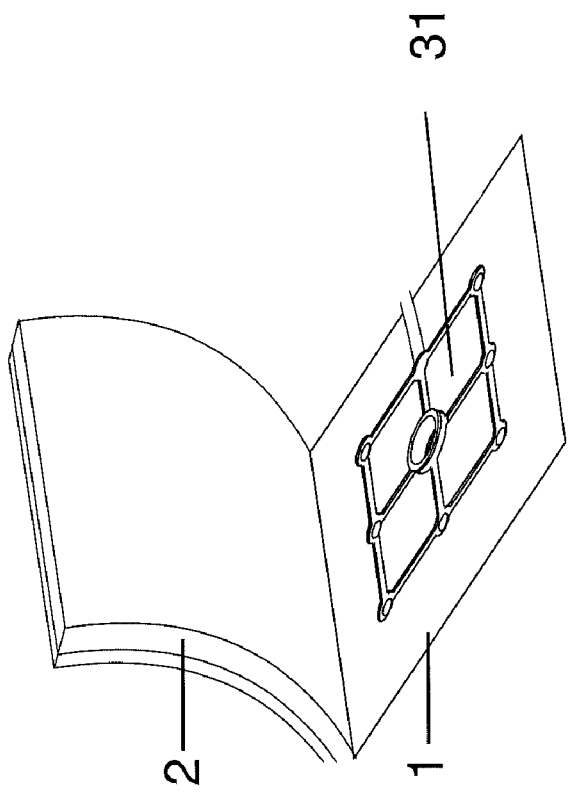
FIG. 3 illustrates a perspective view of the permanent percutaneous electrical connection device of FIG. 2B positioned in the bone structure.

As shown in FIG. 2B, this implant 31 is impacted into the receiving bone site 1 cavity by any appropriate means, such as impaction pins provided on the plate. Preferably, as illustrated in FIG. 3 and FIG. 8A, the plate-implant 31 is anchored in the cavity "L" naturally, i.e. without additional fixation means, for example by cooperation between the walls of the bone cavity and the lateral walls and/or the impaction pins of the plate-implant.

Returning back to FIG. 2B, an impactor 22 adapted to the form of the plate-implant 31 can also be used. Such an impactor 22 is designed for exerting a homogeneous pressure on the plate-implant 31 to help it become anchored in the bone cavity.

Resorbent osteosynthetic screws can also be used, providing additional hold for the plate-implant during the first healing and integration phase. However, such osteosynthetic screws are not compulsory.

In order to facilitate and make durable the osseointegration of the plate-implant 31 in the bone structure, the bone fragments 3 collected during the outer bone table hollowing out phase are positioned on the implant 31 except where the future percutaneous abutment connection area will be. One may also use a bone substitute component.

So that these bone fragments 3 are not dispersed, they are covered with a biocompatible membrane 12 (resorbent or non-resorbent) cut out at the two caps (or screws) for protecting the fixed connection port 35 or ports formed on the plate-implant 31, as shown in FIGS. 2A, 5A and 5B.

Figure 6A:
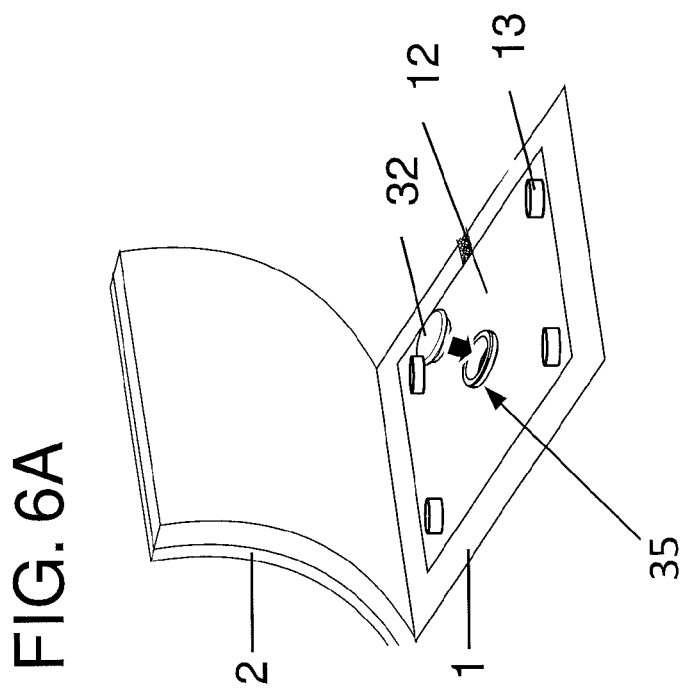
FIG. 6A illustrates a perspective view of a protective cap relative to a fixed electrical port.
Figure 6B:
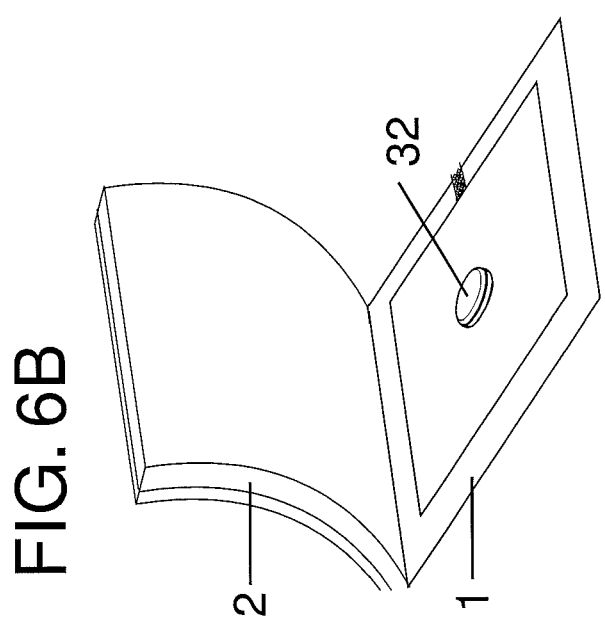
FIG. 6B illustrates a perspective view of the protective cap of FIG. 6A placed at the fixed electrical port.

Preferably, as shown in FIGS. 5C and 6A, this membrane 12 is held in position by osteosynthetic screws 13 distributed around its periphery, so that it is stabilized and bone fragment dispersion is prevented, in order to promote bone proliferation. As shown in FIGS. 6A, 6B and 8B, the membrane 12 is also held where the ports 35 emerge from the plate-implant 31 by a thin plate 34 affixed to the protective cap 32 of the fixed electrical and/or mechanical ports.

More preferably still, the membrane 12 used is PTFE (polytetrafluoroethylene), a non-resorbent material that particularly promotes bone proliferation.

Step 3: Closing the Surgical Site and Bone Integration

The membrane 12 and the plate-implant 31 are then covered by the periosteum 2 and then the skin flap, which is closed after a hematoma drain 4 has been installed, for example a redon or filiform drain, as illustrated in FIG. 8B.

It is possible to perform a subcutaneous soft tissue reduction after this step before suturing. This technical procedure can also be performed during the second surgery phase when the percutaneous abutment is positioned.

The plate-implant can be integrated in the bone wall progressively, over a period of several months, for example three to four months, depending on the type of bone at the receiving site, which can vary from barely mineralized bone to extremely mineralized bone.

This first phase allowing the implant to be correctly integrated in the bone wall is called integration.

Step 4: Positioning the Connection Abutment or Abutments

Figure 7A:
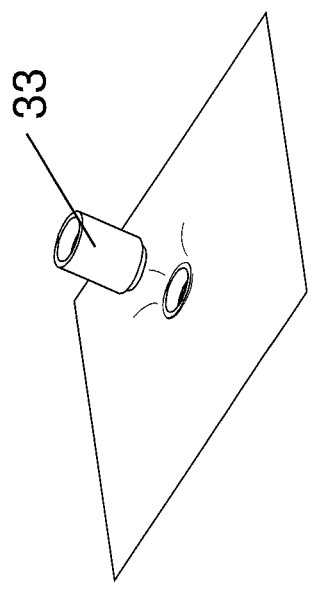
FIG. 7A illustrates a perspective view of an abutment relative to the fixed electrical port.
Figure 7B:
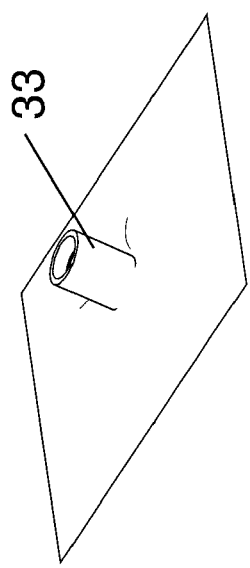
FIG. 7B illustrates a perspective view of the abutment of FIG. 7A placed at the fixed electrical port.

After three to four months of bone healing, the implant 31 may be considered osseointegrated. The second surgical phase can then begin, consisting of positioning the percutaneous elements for permanent percutaneous electrical connection on the implant, said elements being called abutments 33 (electrical and/or mechanical), as illustrated in FIGS. 7A-7B.

This step consists of first preparing a skin flap made hairless by any appropriate treatment (electrical or mechanical depilation, free graft of thin skin, etc.). If a free graft of thin skin is chosen, which is preferable, this is taken beforehand from a hairless skin zone preferred for this type of graft (supraclavicular hollow, inner arm, behind the ear, etc.).

If not done at the end of the first surgical phase, reduction of the subcutaneous soft tissue of the skin flap or free graft of thin skin fragment is done at this stage.

The cutaneous plane is incised depending on the surgical option selected for percutaneous passage of the abutments: thin flap or free graft of free skin.

Before pre-positioning the hairless skin on top of the protective caps for the future abutment connection areas (only areas flush with the plate-implant), the membrane and its fastening means should be removed, i.e. the osteosynthetic screws (if they are not resorbent) and the thin plate holding the membrane at the protective caps for the fixed abutment connection ports.

After having removed the membrane, the skin through which the abutment will cross can be positioned over the implant. The hairless skin positioned over the implant is prestabilized, for example by means of sutures.

Before completely stabilizing the hairless skin, the protective caps for the electrical connection bearing element of the implant and for the possible mechanical connection port are removed. The percutaneous abutments (for electrical and mechanical connection) are presented in order to trace on the skin the area where openings for passage of the abutments will be made.

The abutments are then adjusted and immobilized on the implant, crossing the openings made in the hairless skin area.

The prestabilization sutures are then knotted in order to prevent any movement of the hairless skin around the abutment; the longevity of the percutaneous connection depends essentially on respecting this requirement.

A compression bandage is then positioned so that the cutaneous epithelium over the cranial periosteum can heal and prevent any movement of skin around the abutment.

Description of a Preferred Surgical Protocol

The protocol that follows relates to the positioning of a permanent percutaneous electrical connection device in two operations and with immediate electrical coupling with electrical connection means for an artificial heart.

After an artificial heart is positioned, three months beforehand, and as long as the general condition has improved after positioning an artificial heart temporarily fed by a percutaneous abdominal electric wire, the patient can receive a permanent percutaneous electrical connection. The protocol used for positioning the permanent percutaneous electrical connection device and its electrical coupling to the artificial heart is the following.

A similar protocol may be used for positioning a permanent percutaneous electrical connection device to be connected with an implanted assisted circulation.

Step 0: Preliminary Analysis for Implantation

A prior examination of the receiving bone site is performed by imaging (scanning and x-ray), and by virtual simulated implantation.

A stereolithographic cranial model corresponding to the receiving bone site is then created in order to simulate the future implantation.

Step 1: Preparing the Receiving Bone Site

Firstly, a wide approach is made for the cranial bone plane after bicoronal cutaneous incision, and then the parieto-occipital part of the scalp is lifted and moved back.

Next the periosteum is incised and lifted, and then the bone surface necessary for embedding the implant is cleared.

Next an implant template is affixed on the cleared bone surface by several osteosynthetic screws, possibly self-drilling.

By means of this template, a notch of several millimeters is hollowed in the outer bone table by means of a piezosurgical handpiece (or any other bone cutting means). The template defines a zone to be hollowed out according to an outline corresponding to the shape of the plate-implant, with slightly smaller dimensions in order to permit primary anchoring of the plate-implant in the cavity.

When the delineation of the implant area is finished, this defined area should be hollowed out so as to be able to partially imbed the implant therein.

Various manual or mechanical means can be used to prepare the implant bone site, such as, for example, hand hollowing with a conventional fissure bur or with a fissure bur with depression guard. The bone can also be removed by a bone chisel. The site can also be hollowed out by means of an automated mechanical device.

Regardless of the cutting means used, the bone fragments resulting from the preparation of the site are carefully collected to be used later to facilitate bone proliferation.

The preparation of the receiving site is then checked by means of a model of the implant and the site is adjusted with the template if necessary.

Step 2: Impacting the Implant

When the cavity is perfectly designed to receive the plate-implant, the implant is positioned in the cavity, and is then impacted with the corresponding impactor. This impactor allows anchoring the plate-implant with extreme gentleness so as not to deform the implant, particularly its extensions. The primary anchoring of the plate-implant is done by cooperation of the implant with the lateral walls of the bone cavity.

This primary anchoring may sufficient for fixing the plate-implant. However, as a precaution, it is possible to reinforce this primary anchoring temporarily while osseointegration occurs by temporarily positioning osteosynthetic screws, possibly resorbent ones. If the screws are not resorbent, they are removed in subsequent surgical phase.

The bone fragments collected during the outer table hollowing phase are arranged in contact with the implant, in particular on the upper surface of the plate-implant, except on the area for the electrical and/or mechanical connection of future percutaneous abutments. So that these bone fragments are not dispersed, they are covered with a membrane, ideally in PTFE, cut out opposite the two protective caps (or screws). The membrane is immobilized at its periphery as well as around the two protection caps for the fixed implant connection ports by a metal plate (ideally titanium) affixed on the protective cap. As a result, the membrane ensures a guided bone regeneration.

The aim of this step is to facilitate and make durable the osseointegration, on the one hand, and especially to make the two emerging parts of the permanent percutaneous electrical connection device implant similar to the emerging parts of traditional extraoral (or even dental) implants, i.e. isolated on the bone surface.

Step 3: Closing the Surgical Site and Bone Integration

After immobilization of the membrane, the periosteum is repositioned on the membrane, and then a redon or filiform hematoma drain is installed.

Then the cutaneous plane above the membrane and the periosteum is closed.

After positioning the plate-implant, bone is allowed to proliferate around the implant so that it becomes an integral part of the receiving bone site by osseointegration. This three-month period is called the implant-plate integration period.

Step 4: Positioning the Connection Abutment or Abutments

After a few months of bone healing, the implant is considered osseointegrated. The second surgical procedure is performed, consisting of connecting the implant and the percutaneous part of the permanent percutaneous electrical device through the plane of the skin.

The free graft of thin skin is made in an oblong shape, preferably in the area behind the ear (or in any other area of suitably hairless skin), and of approximately 2.5 cm on its long axis and 1.5 cm on its short axis. The scalp excision is matched against the percutaneous abutments and the skin graft through which the abutments will pass by presenting the graft.

The permanent percutaneous electrical connection device and the artificial heart supply wires (previously placed on standby) can then be connected.

Then the two protective caps are removed from the electrical connection bearing element and the possible mechanical connection port of the implant.

The periosteum is replaced on top of the implant, without covering the electrical connection port, nor the mechanical connection port if present.

The free graft of thin skin is then pre-positioned and held by several unknotted temporary sutures.

The graft is then pierced at the position of the electrical and mechanical abutments.

The two percutaneous abutments are then presented by the two openings made in the skin graft, and they are connected and immobilized on the implant.

Finally, the graft is affixed permanently by tying knots in the sutures used to prestabilize the free graft of thin skin, and a compression bandage is positioned in order to firmly press the reduced graft against the epithelium on the periosteum.

Description of the Specific Equipment Used for Positioning the Implant Plate for Permanent Percutaneous Electrical Connection Any operation for positioning an implant-plate for the permanent percutaneous electrical connection device is preferably preceded by imaging the receiving site: teleradiographs, particularly face and profile, and especially scanning and equipment pre-positioning software. An anatomical stereolithographic reconstruction may possibly be used to visualize the proper placement of the implant-plate for permanent percutaneous electrical connection by means of a template.

Various means, manual or mechanical, can be used to prepare the receiving bone site: fissure bur with depression guard, piezosurgical instrument, etc. This permanent percutaneous electrical connection implant-plate receiving site can also be prepared by automated or robotic means. Regardless of the means used, an irrigation and suction system is preferably provided to collect the bone chips formed during this step.

The implant-plate is impacted with an "impactor", i.e. a tapping instrument perfectly adapted to the upper part of the plate and allowing impacting this plate without deforming it. The implant-plate is impacted into the housing created in the cranial outer bone table (preferably parieto-occipital) by tapping with a hammer (Lombard hammer), (and with care) on the impactor.

The reader will understand that numerous modifications can be introduced without exceeding the scope of the novel disclosures and advantages described here. Consequently, all modifications of this type are included under the scope of the surgical method according to the invention for implanting a permanent percutaneous electrical device in a patient.

The invention claimed is:

1. A surgical method for positioning a permanent percutaneous electrical connection device in a receiving bone site of a patient, the patient being a human being or an animal, and the device comprising, on the one hand, a plate-implant integrating at least one fixed electrical connection port and, on the other hand, a percutaneous electrical connection abutment designed to be coupled to the electrical connection port, the method comprising the following successive steps:

step of preparing the receiving bone site, during which:

the cutaneous plane facing the receiving bone site is incised, then the periosteum of the receiving bone site is incised and detached and then reclined to clear the bone structure, then the bone structure is hollowed out so as to form a cavity in which the plate-implant is to be impacted;

step of impacting the plate-implant into the cavity formed in the receiving bone site, during which:

the plate-implant is anchored in the cavity formed in the receiving bone site, then bone fragments are positioned to cover the plate-implant except in the area of the fixed electrical connection port, then said bone fragments are covered with a membrane to keep the bone fragments in position so as to ensure guided bone regeneration, said membrane being affixed to the bone structure on one part and to the plate-implant on another part in order to hold the bone fragments in position, wherein the membrane covering the bone fragments is affixed to the bone structure on one side by osteosynthetic screws positioned at the membrane periphery.

2. The surgical method of claim 1, wherein, during the receiving bone site preparation step, the bone fragments produced when the bone structure is hollowed out to form the cavity are collected, in order to use these bone fragments during the plate-implant impaction step.

3. The surgical method of claim 1, wherein the step of preparing the receiving bone site is done with permanent irrigation to limit heating of the receiving bone site.

4. The surgical method of claim 1, wherein the bone structure is hollowed out by using a template that enables hollowing a cavity with a form corresponding to the plate-implant outline, said cavity having smaller dimensions so as to provide primary anchoring of the plate-implant in the cavity by cooperation of the corresponding walls.

5. The surgical method of claim 1, wherein the membrane covering the bone fragments is affixed to the plate-implant on one side, via a thin metal plate pressing the membrane around protective caps positioned on the fixed electrical connection port.

6. The surgical method of claim 1, wherein an impaction tool is used with a support surface having a form complementary to the form of the upper surface of the plate-implant, so as to anchor the plate-implant in the bone cavity without deforming said plate-implant.

7. The surgical method of claim 1, further comprising a step of bone integration consisting of covering the membrane and the plate-implant by the periosteum, and then by the skin flap of the patient, after a hematoma drain has been positioned.

8. The surgical method of claim 1, comprising a second surgical phase performed 3 to 4 months after the first surgical phase for positioning the plate-implant, said second surgical phase comprising the following successive steps:

removal of the membrane ensuring guided bone regeneration, removal of a protective cap positioned on the fixed electrical connection port of the plate-implant, then replacement of said protective cap with the percutaneous electrical connection abutment.

9. The surgical method of claim 1, wherein the permanent percutaneous electrical connection device is connected with one or more elements located inside the organism of the patient.

10. The surgical method according to claim 9, wherein the permanent percutaneous electrical connection device is also connected with one or more elements located outside the organism of the patient.

\* \* \* \* \*